United States Patent [19]
Culbreth, III et al.

[11] Patent Number: 6,023,001
[45] Date of Patent: Feb. 8, 2000

[54] PEROXIDE PRODUCTION

[75] Inventors: William K. Culbreth, III, Beaumont; Mark E. Taylor, Magnolia; Kyle L. Preston, Port Arthur; Mark A. Mueller, Austin, all of Tex.

[73] Assignee: Huntsman ICI Chemicals LLC, Austin, Tex.

[21] Appl. No.: 09/040,817

[22] Filed: Mar. 18, 1998

[51] Int. Cl.$^7$ .......................... C07C 409/00; C07C 27/10
[52] U.S. Cl. .......................... 568/571; 568/568; 568/569; 568/910
[58] Field of Search .................... 568/571, 568, 568/569, 910

[56] References Cited

U.S. PATENT DOCUMENTS

| | | | |
|---|---|---|---|
| 2,845,461 | 7/1958 | Winkler et al. | 568/910 |
| 3,478,108 | 11/1969 | Grane | 260/610 |
| 3,907,902 | 9/1975 | Grane | 260/610 B |
| 4,294,999 | 10/1981 | Grane et al. | 568/910 |
| 4,296,262 | 10/1981 | Grane et al. | 568/910 |
| 4,296,263 | 10/1981 | Grane et al. | 568/910 |
| 4,404,406 | 9/1983 | Lutz et al. | 568/571 |
| 4,547,598 | 10/1985 | Sanderson et al. | 568/922 |
| 4,705,903 | 11/1987 | Sanderson et al. | 568/922 |
| 5,093,506 | 3/1992 | Marquis et al. | 568/571 |
| 5,149,885 | 9/1992 | Jubin, Jr. | 568/571 |
| 5,151,530 | 9/1992 | Marquis et al. | 568/571 |
| 5,159,122 | 10/1992 | Sanderson et al. | 568/699 |
| 5,185,480 | 2/1993 | Sanderson et al. | 568/913 |
| 5,220,075 | 6/1993 | Ember | 568/573 |
| 5,243,083 | 9/1993 | Cowley et al. | 568/571 |
| 5,243,084 | 9/1993 | Cochran et al. | 568/571 |
| 5,243,091 | 9/1993 | Kruse et al. | 568/571 |
| 5,334,771 | 8/1994 | Ember et al. | 568/573 |
| 5,395,980 | 3/1995 | Mueller et al. | 568/573 |
| 5,399,777 | 3/1995 | Mueller | 568/569 |
| 5,436,375 | 7/1995 | Thomas et al. | 568/571 |

FOREIGN PATENT DOCUMENTS

| | | |
|---|---|---|
| 076 534 | 4/1983 | European Pat. Off. . |
| 673 907 A1 | 1/1995 | European Pat. Off. . |
| 673 908 A1 | 1/1995 | European Pat. Off. . |
| 32 48 465 A1 | 7/1984 | Germany . |

OTHER PUBLICATIONS

U. S. SN 08/002,563 "Di–tert–butyl peroxide Decomposition Over a Ni–Cu–Cr–Fe on Kieselguhr Catalyst in a Methl tert–butyl ether Recycle Stream," filed Jan. 11, 1993.

*Primary Examiner*—Gary Geist
*Assistant Examiner*—J. Parsa
*Attorney, Agent, or Firm*—O'Keefe, Egan and Peterman

[57] ABSTRACT

Peroxides are prepared from organic compounds and oxygen in a reaction vessel by introducing organic compound and oxygen to the reaction vessel and by simultaneously withdrawing a first liquid product stream from adjacent the top of the reactor and a second liquid product stream from adjacent the bottom of the reaction vessel. Suitable organic compounds include, but are not limited to, alkanes and all aryl compounds.

27 Claims, 2 Drawing Sheets

PEROXIDE PRODUCTION

BACKGROUND OF THE INVENTION

1. Field of the Invention

The present invention relates generally to a peroxidation process for producing peroxides from organic compounds, such as production of alkyl peroxides and/or alkyl aryl peroxides from alkanes and/or alkyl aryl compounds and oxygen. More specifically, this invention relates to production of such peroxides in a reactor in which liquid product streams are withdrawn from locations near the top and bottom of the reactor. In particular, this invention relates to a process for the non-catalytic or auto-catalytic production of tertiary butyl hydroperoxide ("TBHP") and tertiary butyl alcohol ("TBA") from isobutane and oxygen in a vertical reactor in which a first liquid product stream is typically withdrawn from a position adjacent the top of the reactor and a second liquid product stream is typically withdrawn from a position adjacent the bottom of the reactor.

2. Description of Related Art

The non-catalytic or auto-catalytic liquid phase reaction of organic compounds, such as alkanes or alkyl aryl compounds, with molecular oxygen to produce peroxides is commonly performed in reactor vessels. By "auto-catalytic reaction" it is meant that no catalyst is required, either continuously or in a fixed bed. Such peroxidation reaction processes include, for example, peroxidation processes such as those described in U.S. Pat. No. 5,436,375. For example, a vertical or horizontal reactor vessel may be configured to receive a liquid alkane feed through which molecular oxygen is bubbled under reaction conditions to form, for example, alkyl peroxides and/or alcohols. Typically, such reactors are configured with one or more internal weirs for maintaining one or more reactant liquid levels through which molecular oxygen may be bubbled for reaction. Alkyl peroxide and/or alcohol-containing product streams are typically recovered from liquid which overflows the weir. In this regard, one or more weirs may be utilized to maintain a single alkane liquid level within a reactor vessel, or may be configured to maintain sequentially decreasing levels (such as by separating multiple compartments in a horizontal reactor vessel) through which a liquid reactant phase moves by overflowing each sequential weir. In the latter case, oxygen may be injected into each compartment between the weirs.

In peroxidation reactors, compounds such as alkyl peroxides, alkyl aryl peroxides and/or alcohols are typically prepared by sparging oxygen or a mixture of liquid and/or gaseous alkane and/or alkyl aryl with oxygen to the bottom of the reactor and by charging a feed stream of fresh and/or recycled liquid alkane and/or alkyl aryl compound to the top of the reactor, and by withdrawing a liquid weir overflow product stream from a point adjacent the top of the reactor and a vapor product stream from the top of the reactor. For example, in one typical process for the non-catalytic or auto-catalytic production of TBHP and TBA from isobutane and oxygen, a vertical reactor is employed. In this process TBHP and TBA are produced from isobutane and oxygen by sparging a mixture of isobutane with oxygen to the bottom of the reactor, by charging a reaction mixture recycle stream to the reactor above the sparge point, by centrally charging a downwardly flowing stream of cooled isobutane (fresh isobutane, recycled isobutane, or a mixture thereof) to the top of the reactor to induce central downflow of the isobutane and annular upflow of the sparged mixture in the recycle stream, by withdrawing a liquid product stream adjacent the top of the reactor, by withdrawing a vapor product stream from the top of the reactor, by condensing liquids from the vapor product, and by recycling the condensed liquids and recovering the liquid product stream.

In liquid phase peroxidation reactors such as those described above, productivity of peroxide, such as TBHP may suffer over time. With a reduction in peroxide productivity may also come an increase in alcohol (e.g., TBA) production. At the same time, acid number and presence of undesirable byproducts in the liquid product stream typically increases. Such undesirable by-products include methanol, acetone, and other compounds easily oxidized to acid compounds. Other related phenomena may include increased production of carbon monoxide and carbon dioxide which, among other things, may lead to increased pressure in a reactor vessel and which may in turn necessitate reduction in rates due to pressure concerns in the reactor and downstream of the reactor vessel. Therefore, in conventional peroxidation reaction processes, productivity of peroxide may be reduced due to decreased selectivity to peroxide coupled with a reduction in flow rates in order to maintain reactor pressure at an acceptable level. In this regard, design pressure limits are typically dictated by economics and/or construction parameters.

SUMMARY OF THE INVENTION

TBHP and TBA may be prepared from isobutane and oxygen in a vertical reactor by sparging a mixture of isobutane with oxygen to the bottom of the reactor, by charging a reaction mixture recycle stream to the reactor above the sparge point, by centrally charging a downwardly flowing stream of cooled isobutane (fresh isobutane, recycled isobutane, or a mixture thereof) to the top of the reactor to induce central downflow of the isobutane annular and upflow of the sparged mixture and the recycle stream, by withdrawing a first liquid product stream adjacent the top of the reactor, by withdrawing a second liquid product stream adjacent the bottom of the reactor, by withdrawing a vapor product stream from the top of the reactor, by partially condensing entrained liquids in the vapor product, by recycling the condensed liquids and by recovering the liquid product streams.

Therefore, in one respect, this invention is a process for producing peroxide in a reaction vessel, including the steps of introducing an organic compound and oxygen into the reaction vessel so that the organic compound and oxygen react to form peroxide; withdrawing a first liquid product stream including peroxide from adjacent the top of the reactor; and withdrawing a second liquid product stream including alkyl peroxide from adjacent the bottom of the reactor. In this process, the organic compound may be at least one of alkane having from about 4 to about 8 carbon atoms or derivatives thereof, alkyl aryl compound with one or more alkyl groups having from about 2 to about 8 carbon atoms or derivatives thereof, or a mixture thereof. Specific examples of suitable organic compounds include, but are not limited to, at least one of isobutane, isopentane, iso-octane, cyclohexane, ethylbenzene, or a mixture thereof. In the practice of this process, the step of introducing may include sparging a mixture of the organic compound and the oxygen to a point adjacent the bottom of the reaction vessel, and may further include centrally charging a downwardly flowing stream of cooled isobutane (fresh isobutane, recycled isobutane, or a mixture thereof) to the top of the reaction vessel to induce central downflow of the isobutane and annular upflow of the sparged mixture and the recycle stream. The process may further include the step of charging a reaction mixture recycle stream to the reactor above the sparge point The process may also include the step of withdrawing a vapor product stream including the alkane from the top of the reactor. In one embodiment, the first liquid product stream and the second liquid product stream are withdrawn from the reaction vessel in a draw-off ratio of from about 4:1 to about 100:1. In another embodiment, the reaction vessel may be a vertical reactor having length to diameter ratio of at least about 1.1. In one more typical embodiment, the organic compound is isobutane and the peroxide is tertiary butyl hydroperoxide, and the first and second liquid product streams include isobutane, tertiary butyl hydroperoxide, tertiary butyl alcohol and oxygenated hydrocarbon by-products. In one embodiment, the process may further include the step of maintaining a temperature within the reaction vessel of between about 120° C. and about 165° C., and maintaining a pressure within the reaction vessel of between about 380 psig and about 600 psig. In another embodiment, the process may further include the step of maintaining a temperature within the reaction vessel of between about 120° C. and about 165° C., and maintaining a pressure within the reaction vessel of between about 500 psig and about 600 psig.

In another respect, this invention is a process for producing tertiary butyl hydroperoxide in a reaction vessel, including the steps of introducing liquid isobutane and oxygen into the reaction vessel so that the liquid isobutane and the oxygen react to form tertiary butyl hydroperoxide; withdrawing a vapor product stream including isobutane from the top of the reactor; withdrawing a first liquid product stream including tertiary butyl hydroperoxide from adjacent the top of the reactor; and withdrawing a second liquid product stream including tertiary butyl hydroperoxide from adjacent the bottom of the reactor. The step of introducing may include sparging a mixture of the liquid isobutane and the oxygen to a point adjacent the bottom of the reaction vessel, and may further include centrally charging a downwardly flowing stream of cooled isobutane to the top of the reaction vessel to induce central downflow of the isobutane and annular upflow of the sparged mixture and the recycle stream. In one embodiment, the process may further include the step of charging a reaction mixture recycle stream to the reactor above the sparge point. The first liquid product stream and the second liquid product stream may be withdrawn from the reaction vessel in a draw-off ratio of from about 4:1 to about 100:1. In one embodiment, the reaction vessel may be a vertical reactor having length to diameter ratio of at least about 1.1 and, more typically, having a length to diameter ratio of from about 1.1 to about 3. The first and second liquid product streams may include isobutane, tertiary butyl hydroperoxide, tertiary butyl alcohol and oxygenated hydrocarbon by-products. The process may further include the step of maintaining a temperature within the reaction vessel of between about 120° C. and about 165° C., and maintaining a pressure within the reaction vessel of between about 500 psig and about 600 psig.

In another respect, this invention is a process for the production of tertiary butyl hydroperoxide and tertiary butyl alcohol from isobutane and oxygen in a vertical reactor which includes the steps of sparging a mixture of isobutane with oxygen at a point adjacent the bottom of the reactor, charging a reaction mixture recycle stream to the reactor above the sparge point, centrally charging a downwardly flowing stream of cooled isobutane adjacent the top of the reactor to induce central downflow of the isobutane and annular upflow of the sparged mixture and the recycle stream, withdrawing a first liquid product stream adjacent the top of the reactor, withdrawing a second liquid product stream adjacent the bottom of the reactor, withdrawing a vapor product stream including isobutane from the top of the reactor, partially condensing the vapor stream, recycling the condensed isobutane to the bottom of the reactor, and recovering the first and second liquid product streams. In one embodiment, the vertical reactor may have a length to diameter ratio of at least about 1.1, the step of charging a reaction mixture includes charging a reaction mixture recycle stream into the reactor adjacent the bottom thereof and above the sparging point for the mixture of isobutane with oxygen, the step of centrally charging includes the step of centrally charging an isobutane charge stream having a charge stream temperature of about 10° C. to about 55° C. to the reactor, the step of withdrawing a liquid product stream includes withdrawing a liquid product stream adjacent the top of the reactor including isobutane, tertiary butyl hydroperoxide, tertiary butyl alcohol and oxygenated hydrocarbon by-products, the step of withdrawing a vapor product stream includes withdrawing a vapor product stream from the top of the reactor including isobutane and entrained normally liquid reaction products, the step of partially condensing includes cooling the vapor product to condense normal liquid reaction product components thereof, the step of recycling includes recycling the condensed products to the reactor as the reaction mixture reflux stream. This embodiment may further include the steps of establishing reaction conditions within the reactor including a temperature within the range of about 120° C. to about 165° C. and a pressure between about 500 psig and about 600 psig; and recycling uncondensed components of the product vapor stream including isobutane to the reactor in admixture with added oxygen as the sparge mixture. The liquid product stream may be charged to a distillation zone and separated therein into a lower boiling point isobutane fraction and a higher boiling point fraction comprising tertiary butyl hydroperoxide, tertiary butyl alcohol and oxygenated hydrocarbon by-products, and the lighter isobutane fraction may be cooled to a temperature of about 10° C. to about 55° C. and recycled to said reactor as part of the isobutane charge stream.

In another respect, this invention is a process for the non-catalytic or auto-catalytic production of tertiary butyl hydroperoxide and tertiary butyl alcohol from isobutane in a vertical reactor having a length to diameter ratio of from about 1.1 to about 3 to 1 which includes the steps of establishing reaction conditions within the reactor including a temperature within the range of about 120° C. to about 165° C. and a pressure within the range of about 380 to about 600 psig, peripherally sparging about 200 to about 400 parts per hour of a mixture including oxygen and isobutane into the reactor adjacent the bottom thereof, the mixture containing 5 to about 15 parts of oxygen per 100 parts of isobutane, charging about 150 to about 250 parts per hour of a reaction mixture recycle stream into the reactor adjacent the bottom thereof and above the sparging point for the mixture of isobutane with oxygen, centrally charging about 100 parts per hour of an isobutane charge stream having a charge stream temperature of about 10° C. to about 55° C. to the reactor adjacent the top thereof in a downwardly flowing direction to induce central downflow of the isobutane in the reactor and to thereby induce annular upflow of the sparged mixture and the reaction mixture recycle stream, withdrawing about 80 to about 120 parts per hour of a first liquid product stream adjacent the top of the reactor including isobutane, tertiary butyl hydroperoxide, tertiary butyl alcohol and oxygenated hydrocarbon by-products, withdrawing about 1 to about 20 parts per hour of a second liquid product stream adjacent the bottom of the reactor including isobutane, tertiary butyl hydroperoxide, tertiary butyl alcohol and oxygenated hydrocarbon by-products, withdrawing about 350 to about 650 parts per hour of a vapor product stream from the top of the reactor including isobutane and entrained normally liquid reaction products, cooling the vapor product to condense normal liquid reaction product components thereof, recycling the condensed products to the reactor as the reaction mixture recycle stream, recycling uncondensed components of the product vapor stream including isobutane to the reactor in admixture with added oxygen as the sparge mixture, and recovering the first and second liquid product streams. The first and second liquid product streams may include about 10 to about 25 wt. % of tertiary butyl hydroperoxide, about 9 to about 20 wt. % of tertiary butyl alcohol, about 20 to about 75 wt % of unreacted isobutane and about 2 to about 10 wt. % of oxygen-containing impurities including ditertiary butyl peroxide, methanol, methyl formate, acetone and water. In one embodiment, the liquid product stream may be charged to a distillation zone and separated therein into a lower boiling isobutane fraction and a higher boiling fraction comprising tertiary butyl hydroperoxide, tertiary butyl alcohol and oxygenated hydrocarbon by-products, and the lighter isobutane fraction may be cooled to a temperature of about 10° C. to about 55° C. and recycled to the reactor as part of the isobutane charge stream. In another embodiment, the step of establishing includes the step of establishing a pressure of between about 500 psig and about 600 psig in the reactor.

In another respect, this invention is a process for the non-catalytic or auto-catalytic production of tertiary butyl hydroperoxide and tertiary butyl alcohol from isobutane in a vertical reactor having a length to diameter ratio of at least 1:1 is provided which comprises the steps of: establishing reaction conditions within said reactor including a temperature within the range of about 120° C. to about 165° C. and a pressure within the range of about 380 psig to about 600 psig (more typically between about 380 psig and about 530 psig); sparging a mixture of isobutane with oxygen into said reactor adjacent the bottom thereof; charging a reaction mixture recycle stream into said reactor adjacent the bottom thereof and above the sparging point for the said mixture of isobutane with oxygen; centrally charging an isobutane charge stream having a charge stream temperature of about 10° C. to about 55° C. to said reactor adjacent the top thereof in a downwardly flowing direction to induce central downflow of said isobutane in said reactor and to thereby induce annular upflow of said sparged mixture and said reaction mixture recycle stream; withdrawing a first liquid product stream adjacent the top of said reactor comprising isobutane, tertiary butyl hydroperoxide, tertiary butyl alcohol and oxygenated hydrocarbon by-products; withdrawing a second liquid product stream adjacent the bottom of said reactor comprising isobutane, tertiary butyl hydroperoxide, tertiary butyl alcohol and oxygenated hydrocarbon by-products; withdrawing a vapor product stream from the top of said reactor comprising isobutane and entrained normally liquid reaction products; cooling said vapor product to partially condense normal liquid reaction product components thereof; recycling said condensed products to said reactor as said reaction mixture recycle stream; recycling uncondensed components of said product vapor stream, comprising isobutane to said reactor in admixture with added oxygen as said sparge mixture after purging a portion of the uncondensed components prior to recycle; and recovering the liquid product streams.

DESCRIPTION OF ILLUSTRATIVE EMBODIMENTS

Figure 1:
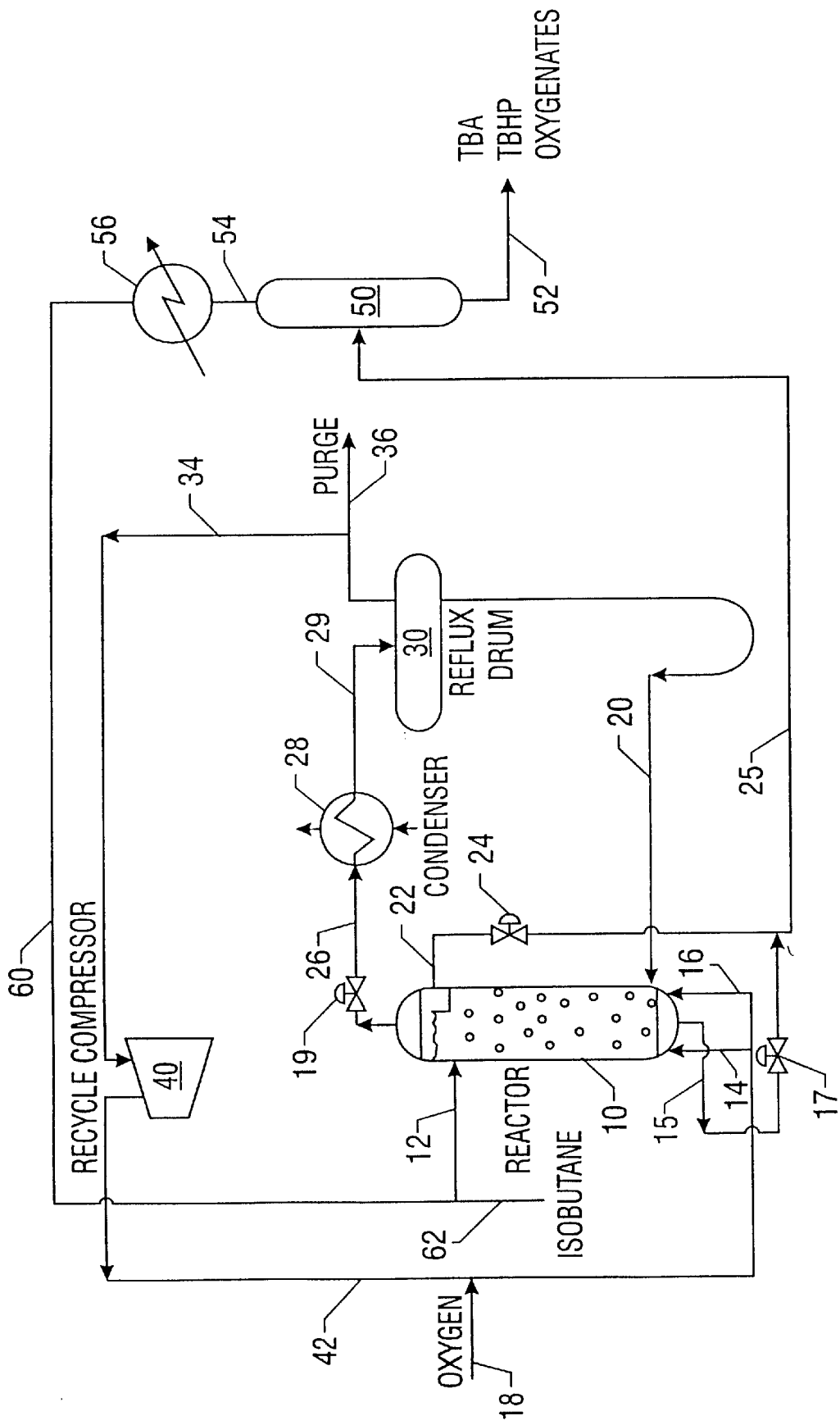
FIG. 1 is a simplified schematic drawing detailing a peroxidation process according to one embodiment of the disclosed method and apparatus including a vertical reactor vessel having dual liquid product streams withdrawn from points adjacent the respective top and bottom of the reactor to vessel.
Figure 4:
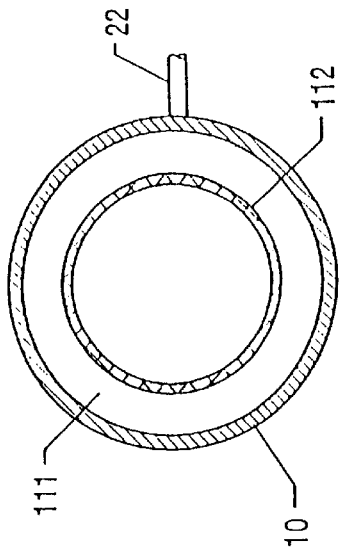
FIG. 4 is a simplified cross-sectional view taken along the lines 4—4 of FIG. 2.

Disclosed herein is a method and apparatus for, among other things, improving selectivity and/or productivity of peroxides in non-catalytic or auto-catalytic liquid phase processes in which liquid alkanes and/or alkyl aryls are reacted with oxygen in reaction vessels. In accordance with the disclosed method and apparatus, reacted liquid product streams are typically withdrawn from at least two outlet lines, one typically adjacent the bottom of a peroxidation reaction vessel. Surprisingly, by withdrawing a portion of the reacted product stream from adjacent the bottom of the reactor, selectivity to peroxide is enhanced. Further advantageously, reaction pressure may be increased allowing improved productivity of peroxide and other desirable by-products such as alcohols. While not wishing to be bound by theory, it is believed that improved selectivity and productivity is promoted by continuously withdrawing a portion of the liquid product stream from a point adjacent the bottom of the reactor which serves to prevent the buildup or accumulation of undesirable catalytic materials (such as, for example, iron, nickel, chromium and their oxides), and/or undesirable reaction by-products, such as high molecular weight oxygenates including, but not limited to, acids, alcohols, aldehydes, ketones or other compounds readily oxidized to such compounds, etc. When present, these undesirable catalytic materials and by-products are believed to, among other things, promote undesirable reactions and cause increased carbon monoxide and carbon dioxide gas production. By removing only a portion of the liquid product stream from a point adjacent the bottom of the reactor, accumulation of such undesirable by-products and catalytic materials may be substantially prevented, while at the same time preventing excessive loss of unreacted oxygen from a reactor vessel through a secondary liquid product draw-off line by removing a major portion of the liquid product from a primary product liquid product draw-off line. Other advantages offered by the disclosed method enhanced stability of a peroxidation system and decreased $CO_2$.

In a typical embodiment, productivity of a peroxidation process is typically improved by removing at least one product stream from a location adjacent the bottom of a peroxidation reactor. More typically, product streams are removed from locations adjacent the top and bottom of a reaction vessel. In such an embodiment, when referred to in regard to a primary product stream, "adjacent the top" of the reaction vessel means that the material is withdrawn from a section of the reactor substantially depleted of oxygen, and when referred to in regard to a secondary product stream, "adjacent the bottom" of the reaction vessel means that the material is withdrawn from a portion of the reactor where solids or dense phase material would tend to accumulate. However, to obtain benefit of the disclosed method and apparatus it is only necessary that a primary liquid product outlet be positioned in a predominantly liquid portion of the reactor and a secondary product outlet be positioned at or below the level of introduction of reactants, such as at or below the level of a sparger. Typically, a majority of the total liquid product produced in the reactor is withdrawn from one or more first or primary liquid product outlets adjacent the top of a reaction vessel, and the balance of liquid product removed from one or more second or secondary liquid product outlets adjacent the bottom of the reaction vessel. In this regard, ratio of the volume of liquid product withdrawn from one or more primary liquid product outlets to volume of liquid product withdrawn from one or more secondary liquid product outlets (defined herein as "draw-off ratio") may be any suitable ratio for obtaining desired peroxide selectivity and/or productivity. In one typical embodiment for production of TBHP in a vertical reactor, the draw-off ratio is typically at least about 4, more typically between about 4 and about 100, even more typically between about 6 and about 90, even more typically between about 15 and about 70, even more typically between about 15 and about 60, and most typically between about 15 and about 50. Minimum draw-off ratio typically depends on factors related to individual reactor configuration, such as loss of oxygen through the secondary liquid product outlet.

Advantageously, the disclosed process and reactor apparatus may be used to increase selectivity and productivity of alkyl peroxides, for example TBHP produced from the reaction of liquid isobutane and molecular oxygen. Other benefits provided by the disclosed method and apparatus include the reduction of product acidity and undesirable by-products, such those is undesirable reaction by-products mentioned above. Furthermore, the disclosed method and apparatus may be used to achieve a more stable peroxidation reaction process in which the number of upsets and/or undesirable pressure increases is minimized. In one embodiment of the disclosed method, increased pressure (i.e., greater than about 500 psig and more typically at least about 520 psig) may be employed in combination with primary and secondary liquid product lines to further enhance the aforementioned benefits.

Streams or feeds which may be reacted with oxygen to produce peroxides include any hydrocarbons or other organic compounds suitable for peroxidation including, but not limited to, alkanes and alkyl aryl compounds. More typically such compounds include, but are not limited to, alkanes having from about 4 to about 8 carbon atoms, alkyl aryl compounds with one or more alkyl groups having from about 2 to about 8 carbon atoms (such as alkyl benzenes with an alkyl group having from about 2 to about 8 carbon atoms), and derivatives and/or mixtures thereof. When alkanes are employed, iso- or branched isomers are typically used. Specific examples of suitable compounds include, but are not limited to, isobutane, isopentane, iso-octane, cyclohexane, ethylbenzene, as well as mixtures and/or derivatives thereof. In one typical embodiment, isobutane is oxidized with molecular oxygen to produce TBHP and TBA. In this regard, typical reaction conditions are described herein for the production of TBHP and TBA from isobutane and oxygen. However, those of skill in the art having benefit of this disclosure will understand that other suitable reaction conditions may be employed to produce other alkyl peroxides from other alkanes using the disclosed method and apparatus.

With benefit of this disclosure those skilled in the art will appreciate that a wide variety of reaction conditions and process steps may be employed to produce alkyl peroxides from alkanes and oxygen. In this regard, conditions and process steps may be varied to suit various reactor types and sizes, process configurations, reactants and desired product characteristics. A non-catalytic or auto-catalytic peroxidation process typically includes the steps of establishing reaction conditions within a reaction vessel; introducing oxygen into the reaction vessel adjacent the bottom thereof; introducing an alkane charge stream to the reactor; withdrawing a liquid product stream adjacent the top of the reactor comprising alkane, alkyl peroxide, alcohol, and oxygenated hydrocarbon by-products; withdrawing a liquid product stream adjacent the bottom of the reactor comprising alkane, is alkyl peroxide, alcohol, and oxygenated hydrocarbon by-products; and withdrawing a vapor product stream from the top of the reactor comprising alkane and any entrained liquid reaction products; and recovering and combining the primary and secondary liquid product streams to form a combined liquid product stream.

In the practice of the disclosed method, a peroxidation reactor vessel may be any reaction vessel suitable for liquid phase oxidation of alkanes, and reactants such as liquid alkanes and oxygen may be introduced into the reaction vessel in any number of suitable ways known to those of skill in the art, including by charging, sparging, etc. Typically, a peroxidation reactor vessel has a liquid alkane feed inlet adjacent the top of a reaction vessel, an oxygen inlet adjacent the bottom of the vessel, one or more internal weirs for maintaining a reactant liquid level in the reactor vessel, a primary liquid product effluent outlet configured to withdraw product effluent overspilling the one or more weirs, a vapor outlet near the top of the vessel and a secondary or purge liquid product effluent outlet adjacent the bottom of the reactor vessel for withdrawing liquid product. Examples of suitable reaction vessel types include vertical reactors, horizontal reactors and/or compartmentalized reactors. In one possible configuration, a vertical reactor having an annular weir system may be employed. Other possible configurations include a compartmentalized horizontal reactor vessel having sequential weirs.

It will be understood with benefit of the present disclosure that a reaction vessel may have, among other things, one or more feed inlets, oxygen inlets, vapor outlets, primary product effluent outlets, and/or secondary product effluent outlets. It will also be understood that position of each such inlet and/or outlet may be varied within any given reactor configuration, although a vapor outlet is typically located near the top of a reaction vessel and a secondary product effluent outlet is typically located near the bottom of the reactor vessel. Location of a primary product effluent outlet may vary, as internal liquid level of the liquid reactant phase is maintained by one or more internal weirs. An example of a conventional peroxidation process and reaction vessel having a single liquid product outlet adjacent the top of the vessel is described in U.S. Pat. No. 5,436,375, which is incorporated herein by reference. One most typical embodiment of the disclosed method and apparatus for production of TBHP and TBA from isobutane and oxygen employs at least one secondary product effluent outlet in combination with such a reaction vessel and process.

In one embodiment of the disclosed method and apparatus, TBHP and TBA are produced from isobutane and oxygen as follows. Liquid isobutane is charged to an oxidation reactor along with oxygen, and oxidation reaction conditions are established therein. In this regard, reaction conditions may include any temperature and pressure suitable for reacting isobutane with oxygen to produce, among other things, TBHP and TBA. Typically, a reaction temperature of above about 120° C., more typically between about 120° C. and about 165° C., even more typically between about 130° C. and about 165° C., even more typically between about 140° C. and about 150° C., and most typically between about 145° C. and about 150° C. is employed. Reaction pressures may similarly vary but are typically between about 380 psig and about 600 psig, and more typically between about 475 psig and about 550 psig. In this embodiment, a portion of isobutane is non-catalytic or auto-catalytically converted to oxidation products including, but not limited to, TBA, TBHP, and minor amounts of oxygen-containing by-products including, for example, ditertiary butyl peroxide, methanol, methyl formate, acetone and water.

In this embodiment, a secondary liquid product effluent outlet is typically located adjacent the bottom of a peroxidation reactor and a primary liquid product effluent outlet is located at a position above the secondary liquid product outlet, although any other location/s of primary and/or secondary liquid product outlets as described elsewhere herein may also be employed. In this embodiment, the liquid product draw-off ratio is typically greater than about 4, more typically between about 4 and about 100, even more typically between about 6 and about 90, and most typically between about 15 and about 50. Typically, the combined liquid product mixture of the primary and secondary product lines comprises greater than about 8 weight percent, more typically greater than about 10 weight percent, and most typically greater than about 12 weight percent of TBHP. More typically, such a combined liquid product mixture also comprises greater than about 6 weight percent, more typically greater than about 8 weight percent, and most typically greater than about 10 weight percent of TBA. Even more typically, such a combined liquid product mixture comprises between about 10 weight percent to about 25 weight percent (even more typically between about 12 weight percent and about 15 weight percent) of TBHP, between about 9 weight percent to about 20 weight percent (even more typically between about 9 weight percent and about 11 weight percent) TBA, between about 20 weight percent to about 75 weight percent (even more typically between about 50 weight percent and about 75 weight percent) unreacted isobutane, and between about 2 weight percent to about 10 weight percent (even more typically between about 2 weight percent and about 5 weight percent) of oxygen-containing impurities. Even more typically, such a combined liquid product mixture comprises about 14 weight percent TBHP, about 11 weight percent TBA, about 70 weight percent unreacted isobutane, and about 5 weight percent of oxygen-containing impurities.

As previously described, the disclosed method may be employed with any non-catalytic or auto-catalytic peroxidation reaction vessel having an internal configuration for maintaining a liquid reactant level, and a liquid product effluent outlet for taking or removing liquid product from a point at or near the upper surface of such a liquid reactant level. However, in a typical embodiment, non-catalytic or auto-catalytic production of TBHP and TBA from isobutane and oxygen occurs in a vertical reactor, and more typically in a vertical reactor having a typical length to diameter ratio of at least about 1.1, and most typically from about 1.1 to about 3.

A non-catalytic or auto-catalytic peroxidation process typically includes the steps of establishing reaction conditions within a reaction vessel, including a temperature of greater than about 120° C. (more typically between about 120° C. and about 165° C., even more typically between about 130° C. and about 165° C., even more typically between about 140° C. and about 150° C., and most typically between about 145° C. and about 150° C.) and a pressure within the range of from about 380 psig and about 600 psig (and more typically between about 475 psig and about 550 psig); introducing about 5 to about 15 (more typically from about 8 to about 15) parts per hour of oxygen into the reaction vessel adjacent the bottom thereof; introducing about 100 parts per hour of an isobutane charge stream to the reactor; withdrawing about 80 to about 120 (more typically about 95 to about 110) parts per hour of a liquid product stream adjacent the top of the reactor comprising isobutane, TBHP, TBA and oxygenated hydrocarbon by-products; withdrawing from about 1 parts per hour to about 20 parts per hour of a liquid product stream adjacent the bottom of the reactor comprising isobutane, TBHP, TBA, and oxygenated hydrocarbon by-products; and withdrawing from about 350 to about 650 parts per hour of a vapor product stream from the top of the reactor comprising isobutane and entrained normally liquid reaction products, and recovering and combining the primary and secondary liquid product streams to form a combined liquid product stream.

In a more typical embodiment, a vertical reactor-based process typically includes the steps of establishing reaction conditions within the reactor including a temperature greater than about 120° C. and more typically within the range of from about 130° C. to about 165° C., and a pressure within the range of about 380 psig to about 600 psig, peripherally (typically uniformly across the cross section of the reactor vessel) sparging about 200 parts per hour to about 400 parts per hour of a mixture comprising oxygen and isobutane into the reactor adjacent the bottom thereof, the mixture containing about 5 to about 15 parts of oxygen per 100 parts of isobutane, charging about 150 to about 250 parts per hour of a reaction mixture recycle stream into the reactor adjacent the bottom thereof and above the sparging point for the mixture of isobutane with oxygen, centrally charging about 100 parts per hour of an isobutane charge stream having a charge stream temperature of about 10° C. to about 55° C. to the reactor adjacent the top thereof in a downwardly flowing direction to induce central downflow of the isobutane in the reactor and to thereby induce annular upflow (or back mixing) of the sparged mixture and the reaction mixture recycle stream, withdrawing about 80 to about 120 (more typically about 95 to about 110) parts per hour of a liquid product stream adjacent the top of the reactor comprising isobutane, TBHP, TBA and oxygenated hydrocarbon by-products, withdrawing from about 1 parts per hour to about 20 parts per hour of a liquid product stream adjacent the bottom of the reactor comprising isobutane, TBHP, TBA, and oxygenated hydrocarbon by-products, withdrawing about 350 to about 650 parts per hour of a vapor product stream from the top of the reactor comprising isobutane and entrained normally liquid reaction products, cooling the vapor product to condense normal liquid reaction product components thereof recycling the condensed products to the reactor as the reaction mixture recycle stream, recycling uncondensed components of the product vapor stream comprising isobutane to the reactor in admixture with added oxygen as the sparge mixture, and recovering and combining the primary and secondary liquid product streams to form a combined liquid product stream. In this embodiment the combined liquid product stream typically comprises between about 10 wt % and about 25 wt % (more typically between about 12 wt. % and about 15 wt. %) of TBHP, between about 9 wt % and about 20 wt. % (more typically between about 9 wt. % and about 11 wt %) of TBA, between about 20 wt. % and about 75 wt. % (more typically between about 50 wt. % and about 75 wt %) of unreacted isobutane and between about 2 wt. % and about 10 wt. % (more typically between about 3 wt. % and about 5 wt. %) of oxygen-containing impurities including ditertiary butyl peroxide, methanol, methyl formate, acetone and water.

In the practice of the above-described embodiment of the disclosed method and apparatus, the primary and secondary liquid product streams from a vertical reactor as described above may be combined and then charged to a distillation zone and separated therein into a lower boiling isobutane fraction and a higher boiling fraction comprising TBHP, TBA and oxygenated hydrocarbon by-products. The lighter isobutane fraction is typically cooled to a temperature of between about 10° C. and about 55° C. and recycled to the reactor as the isobutane charge stream. In this regard, the combined liquid reaction product may be separated in any suitable manner (e.g. by distillation) so as to provide a first lighter isobutane recycle distillation fraction and a first heavier liquid distillation fraction substantially free from isobutane. Such a first heavier liquid distillation fraction typically comprises between about 40 wt. % to about 55 wt % of TBHP, between about 45 wt. % and about 50 wt. % of TBA and between about 3 wt. % and about 5 wt % of oxygen-containing impurities. If so desired, TBA or some other compatible diluent may be added to reduce TBHP concentration in the liquid.

In a most typical embodiment, a vertical reactor-based process typically includes performing the above steps and establishing the same reaction conditions described above, with the exception that a pressure greater than about 500 psig, (more typically between about 500 psig and about 600 psig, or alternatively between about 500 psig and about 530 psig), more typically greater than about 520 psig (more typically between about 520 psig and about 600 psig), and even more typically between about 520 psig and about 530 psig is established within the reactor vessel. Advantageously, such higher pressure further increases TBHP selectivity and productivity over conventional noncatalytic or auto-catalytic processes for producing TBHP from isobutane and oxygen in a vertical reactor. For example, in this embodiment the combined liquid product stream typically comprises between about 12 wt. % and about 15 wt % of TBHP, between about 10 wt % to about 13 wt. % of TBA, between about 65 wt. % and about 75 wt. % of unreacted isobutane and between about 3 wt. % and about 4 wt. % of oxygen-containing impurities including ditertiary butyl peroxide, methanol, methyl formate, acetone and water. In accordance with this high pressure embodiment, the primary and secondary liquid product streams from a vertical reactor as described above may be combined and distilled or otherwise separated as described above into a lighter, lower boiling isobutane fraction and a heavier, higher boiling fraction comprising TBHP, TBA and oxygenated hydrocarbon by-products. In this high pressure embodiment, such a first heavier liquid distillation fraction typically comprises between about 40 wt. % to about 55 wt. % of TBHP, between about 45 wt. % and about 50 wt. % of TBA and between about 3 wt % and about 5 wt % of oxygen-containing impurities.

As illustrated by Example 1, utilization of the disclosed secondary liquid product draw-off line adjacent the bottom of a reactor vessel may be used to increase the selectivity to TBHP by an amount greater than about 3% selectivity, more typically by an amount greater than about 4% selectivity. Furthermore, in another embodiment of the disclosed method illustrated in Example 2, by utilizing a secondary liquid product outlet in conjunction with a reaction pressure of at least about 500 psig (more typically greater than about 520 psig), TBHP selectivity may be further increased by an amount greater than about 2% selectivity and more typically greater than about 3% selectivity. Therefore, by combining a secondary liquid product outlet with relatively high pressures of at least about 520 psig, TBHP productivity may be substantially enhanced over a conventional peroxidation reactor operating at pressures below about 500 psig. In one exemplary vertical reactor embodiment, isobutane selectivity to TBHP utilizing a pressure below about 500 psig and no secondary liquid product outlet, is from about 36% to about 42%. For the same process utilizing a pressure above about 500 psig and a secondary product outlet, isobutane selectivity to TBHP is from about 46% to about 49%.

However, as illustrated in Example 1, increased TBHP productivity may also be achieved at pressures below about 500 psig when compared to conventional reactor vessels lacking a secondary liquid product outlet. Significantly, Example 2 shows that relatively higher pressures (ie., above about 515 psig) in a conventional vertical reactor process does not result in substantial increase in TBHP productivity as exhibited when a secondary liquid product outlet is employed with the same higher pressures. Instead, higher pressures in a conventional reactor tend to increase the productivity of less desirable TBA.

In a vertical reactor embodiment, such as that illustrated in FIGS. 1–5, a vertical reactor is configured so that a sparged mixture of isobutane and oxygen is peripherally charged (or uniformly charged across the reactor cross section) adjacent the bottom of the vertical reactor in an upwardly flowing direction and mixes with and is diluted by the reaction mixture recycle stream and is also mixed with and further diluted adjacent the bottom of the vertical reactor by the downwardly centrally flowing stream of cooled isobutane (which may be fresh isobutane, recycled isobutane, or a mixture thereof). This may be accomplished when the isobutane charge stream is significantly cooler than the circulating reaction mixture. This stream, being initially cooler and denser than the reaction mixture tends to flow or sink towards the bottom of the vertical reactor and the displaced liquid tends to flow upwardly and annularly of the downwardly flowing stream, establishing a convection current. This, in turn, promotes enhanced mixing of reaction mixture components adjacent the bottom of the vertical reactor. Introduction of the cooled isobutane feed stream into the vertical reactor below an annular draw-off tray for the liquid reaction product tends to diminish the likelihood of a break-through of unreacted oxygen into the vapor space at the top of the tower and thus further diminish the likelihood of spontaneous combustion of oxygen and hydrocarbons in the vapor space.

Referring now to the particular and exemplary embodiment shown in FIG. 1 of the drawing, there is schematically shown a vertically mounted oxidation reactor 10 (typically having a length to diameter ratio of least about 1.1, more typically between about 1.1 and about 3) to which a mixture of isobutane with oxygen is continuously sparged by sparge lines 14 and 16 adjacent to the bottom thereof In one typical embodiment, the diameter of a vertical reactor is from about 20 to about 50 feet, and the height of the reactor about 66 feet In this embodiment, a reaction mixture reflux stream is continuously charged to the reactor 10 by line 20 at an injection point adjacent the bottom of the reactor 10 and above the point at which the sparge lines 14 and 16 enter the reactor. Isobutane is centrally continuously charged to reactor 10 in a downwardly flowing direction by an isobutane charge line 12 near the upper liquid level.

Reaction conditions are established within the reactor 10, including a typical temperature within the range of from about 120° C. to about 165° C. and a pressure within the range of from about 380 psig to about 600 psig, more typically a temperature within the range of from about 135° C. to about 165° C. and a pressure within the range of from about 450 psig to about 550 psig, and most typically a temperature within the range of about 140° C. to about 150° C. (even more typically between about 145° C. and about 150° C.) and a pressure within the range of from about 520 psig to about 530 psig.

As shown for the embodiment of FIG. 1, an upper or primary liquid product stream is continuously withdrawn from reactor 10 by a line 22 adjacent the top thereof. A vapor product stream comprising isobutane is continuously withdrawn from the top of the reactor 10 by a line 26. A lower or secondary liquid product stream is continuously withdrawn from reactor 10 by a line 15 adjacent the bottom thereof.

Figure 3:
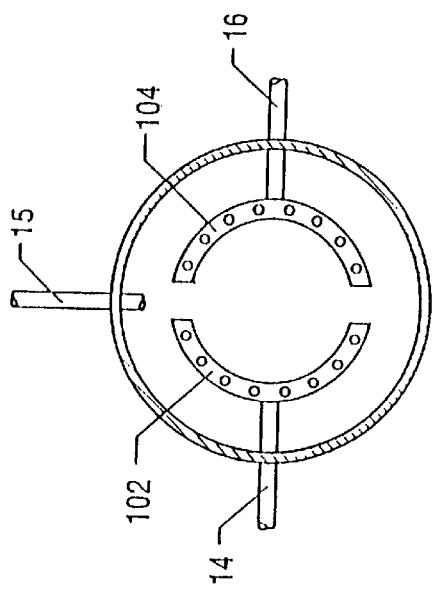
FIG. 3 is a simplified cross-sectional view taken along the lines 3—3 of FIG. 2.
Figure 2:
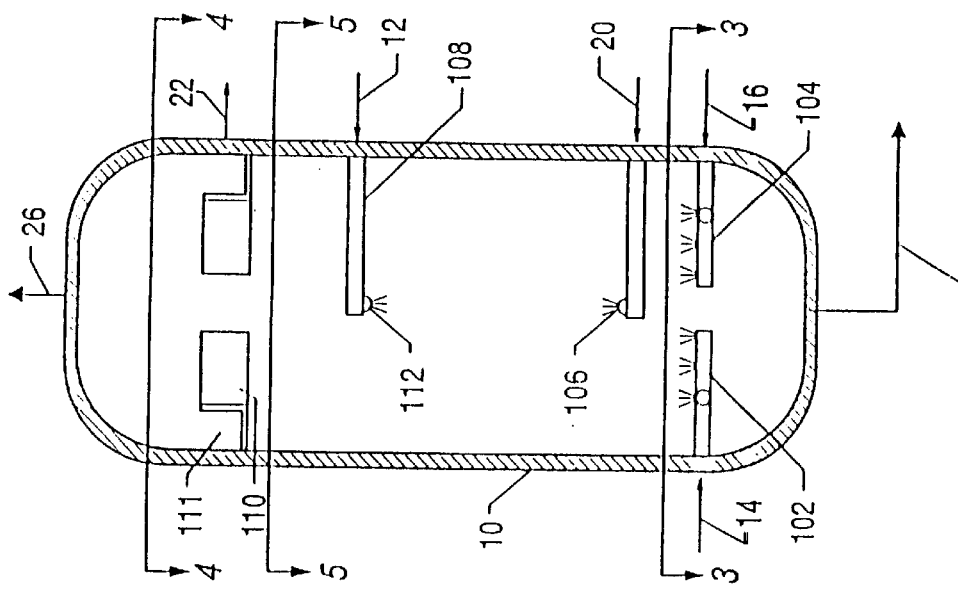
FIG. 2 is a simplified cross-section of the vertical reactor according to the embodiment shown in FIG. 1.

With reference to FIGS. 2 and 3 of the drawings, it will be noted that for this particular embodiment, the mixture of oxygen and butane that is charged to reactor 10 is typically charged by sparge lines 14 and 16 that are connected with corresponding semi-circular shaped spargers 102 and 104 so that the mixture is charged peripherally of the reactor 10 in an upwardly flowing direction.

With further reference to FIG. 2 it will be noted that the reaction mixture recycle stream is charged to reactor 10 by line 20 and typically injected upwardly into reactor 10 by nozzle 106.

Figure 5:
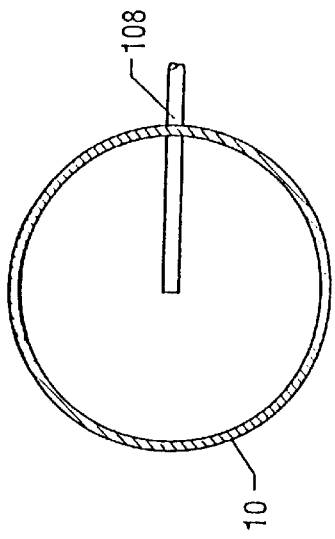
FIG. 5 is a simplified cross-sectional view taken along the lines 5—5 of FIG. 2.

With additional reference to FIG. 2 and to FIG. 5, it will be noted that the cooled isobutane is charged to reactor 10 by line 12 and injected into reactor 10, typically by a downwardly facing isobutane discharge nozzle 112.

With this arrangement, the cooled isobutane, being denser, and because of the direction at which it is introduced tends to continuously flow, or "sink" towards the bottom of the reactor 10 where it will meet and tend to mix with the upwardly flowing warmer reaction mixture recycle stream and with the upwardly flowing oxygen-isobutane mixture that is peripherally introduced through spargers 102 and 104.

As a consequence, a convection current is established and maintained within reactor 10 which is defined by the downwardly flowing stream of cooled isobutane and the peripherally, or annularly upwardly flowing stream of recycled reaction mixture, oxygen and isobutane.

A portion of the reaction mixture continuously flows from the convection current to the top of the reactor 10 where the gaseous components of the reaction mixture continuously exit through the top of the reactor 10 by vapor product streamline 26. As shown in FIG. 1, vapor product stream line 26 is typically provided with a flow control valve 19 which is typically connected to a flow controller (not shown).

An annular liquid draw-off tray 110 defining an annular collecting baffle or weir 111 is mounted in the reactor 10 adjacent to the top thereof (for example about 59 feet from the upper end of a vertical reactor having a length of 66 feet) and the degassed liquid reaction mixture components flow continuously across the baffle 111 into the collecting tray 110 and thence from the reactor 10 through upper or main liquid product outlet draw-off line 22, which is positioned at a level adjacent annular collecting baffle or weir 111. Main product stream draw flange 22 is typically provided with a pressure reduction control valve 24 which is typically coupled to a pressure controller (not shown).

A lower or secondary liquid product stream line 15 is typically provided at the bottom of reactor 10 (typically at the centerline or centerpoint of the bottom of the reactor vessel) through which a portion of the liquid reaction mixture components flow continuously. As shown in FIG. 1, lower liquid product stream line 15 is provided with a flow control valve 17, typically connected to a flow controller (not shown).

In the typical operation of this embodiment of the disclosed method and apparatus, the draw-off ratio of liquid product stream withdrawn from primary liquid product stream draw-off line 22 to secondary liquid product stream draw-off line 15 is typically maintained at a volume ratio of between about 4 to about 90, more typically between about 6 and about 70, and most typically between about 15 and about 60. In this regard, the liquid product stream draw-off ratio is typically controlled using control valves 17, 19, and 24. For example, the vapor flow rate through the vapor product stream line 26 and the liquid flow rate through secondary product stream draw-off line 15 may be set using flow controllers coupled to flow control valves 19 and 17 respectively. The flow rate of liquid product withdrawn from main product stream draw-off line 22 is typically controlled is by pressure controller coupled to control valve 24. Thus, a substantially constant liquid flow rate through line 15 is maintained while liquid product flow rate through lines 22 is adjusted as necessary to maintain the pressure within reactor 10 of the desired range. This is typically so because relatively more vapor is withdrawn from reactor 10 through liquid product stream line 22 when control valve 24 is opened to a greater extent.

Although one embodiment for controlling liquid product draw-off ratio between a primary liquid product draw-off stream and a secondary liquid product draw-off stream is described and illustrated above, it may also be accomplished using any other suitable method known to those of skill in the art including, but not limited to, process control based on measurement of oxygen in downstream towers or process equipment and reducing liquid product draw-off ratio to limit same, measurement of impurities in a secondary liquid product line (such as by visual inspection of product color) and increasing liquid draw-off ratio to reduce darker color, general unit performance (such as peroxide selectivity or peroxidate acid number) and varying liquid draw-off ratio to optimize same, etc.

In this particular illustrated embodiment, the gaseous reaction components that are discharged by vapor product stream line 26, are passed through a condenser 28 where they are partially liquefied and then by line 29 to a reflux drum 30. The condensed liquid components of the reaction mixture are returned to the reactor 10 by reaction mixture recycle line 20 in the described manner. The remaining vapors, mostly vaporized isobutane, are withdrawn from the reflux drum 30 by line 34. A minor portion of the stream 34, e.g., from about 0.5 to about 10 wt %, more typically about 0.5 to about 5 wt. % is purged from the system by purge line 36. The balance of the stream 34 is charged to a recycle compressor 40 where it is repressured to reactor pressure. The repressured stream 42 is directed to sparge lines 14 and 16. Fresh oxygen is mixed with the stream 42, being charged by line 18 in an amount such that the resultant mixture contains about 3 to 10 mol % of oxygen.

The liquid product stream withdrawn from reactor 10 by way of annular draw off tray 110 is discharged by liquid product line 22 that leads to pressure reduction valve 24 where the stream is reduced to substantially atmospheric pressure. The depressured product stream is discharged from valve 24 by a line 25 leading to a distillation zone 50 that may comprise one or a plurality of distillation towers, typically a single atmospheric tower, where it is fractionated to provide a lower boiling isobutane fraction that is discharged by line 54 and a higher boiling fraction discharged by line 52 ; the higher boiling fraction comprising, for example, about 40 wt. % to about 55 wt. % of TBA, about 35 wt. % to about 45 wt. % of TBHP and about 3 wt % to about 5 wt % of oxygenates (i.e., oxygen-containing compounds such as acetone, methyl formate, methanol, ditertiary butyl peroxide, water, etc.).

In this embodiment, the isobutane fraction 54 is typically charged to a heat exchanger 56 where it is cooled to a suitable temperature (e.g., a temperature of about 10° C. to about 55° C.) and it is then charged by line 60 to isobutane charge line 12. Fresh isobutane, as needed, is charged to line 12 by line 62.

Although FIG. 1 illustrates one particular embodiment of a peroxidation process stream employing a condenser, recycle lines, and distillation column, these components are not necessary for obtaining the benefit of the disclosed methods and apparatus. All that is necessary is that a peroxidation reactor be provided with at least one primary liquid product outlet and at least one secondary liquid product outlet as described elsewhere herein. In this regard, although a secondary liquid product outlet stream has been illustrated adjacent the bottom and on the side of a vertical reactor, it will be understood with benefit of this disclosure that a secondary liquid product outlet may be positioned at any other point in the reactor, as long as it is so positioned beneath a primary liquid product outlet and at a point at or below the lowermost point of introduction of reactants. For example, a secondary liquid product outlet may be positioned in the bottom of a reactor, or alternatively may be positioned closer or adjacent to any point intermediate between a primary liquid product outlet and the bottom of the reactor. However, optimal selectivity and productivity is typically obtained when a secondary liquid product outlet is positioned in the bottom or adjacent the bottom of the reactor vessel as illustrated in the figures. Furthermore, it will be understood that more than one secondary liquid product outlets and/or more than one primary liquid product outlets may be employed.

EXAMPLES

The following examples are illustrative and should not be construed as limiting the scope of the invention or claims thereof.

Example 1
TBHP Production with and without Secondary Liquid Product Outlet

Table I illustrates production data taken from a peroxidation process for producing TBHP and TBA from isobutane and oxygen employing two vertical reactors operating in parallel. The process and reactors employed were similar to that illustrated in FIGS. 1–5. Reactor conditions and relative rates of reactant feed and liquid product ratio are illustrated with and without liquid product draw-off (or "purge") through a secondary liquid product outlet.

As may be seen in Table I, at higher pressures (above 500 psig) providing a secondary liquid product outlet substantially decreases the peroxidate acid number and increases isobutane selectivity to TBHP.

Example 2
TBHP Production Under High Pressure Conditions

For the peroxidation process of Example 1, reaction data for low pressure conditions (below 500 psig) and high pressure conditions (above 500 psig), both with and without secondary liquid product draw-off, are also presented.

As may be seen in Table I, at higher pressures, isobutane selectivity to TBHP is increased, while a lower acid number is achieved, as compared to low pressure conditions.

TABLE I

PEROXIDATION PERFORMANCE

| | High Pressure | | Low Pressure | |
| --- | --- | --- | --- | --- |
| Description | Purge | No Purge | Purge | No Purge |
| Oxygen Feed, Parts | 9.1 | 9.9 | 9.3 | 8.9 |
| Isobutane Feed[1], Parts | 100 | 87.3 | 99.5 | 99.7 |
| TBHP/TBA Ratio, p/p | 1.2 | 0.9 | 0.93 | 1.00 |
| Avg Reactor Temp., °F. | 293 | 294 | 291 | 288 |
| Peroxidate Acid Number, mg KOH/g | 11.5 | 19.5 | 15.7 | 15.1 |
| Avg Reactor Pressure, PSIG | 520 | 524 | 475 | 475 |
| Reactor #1 Purge Rate, Parts | 3.4 | N/A | 4.3 | N/A |
| Reactor #2 Purge Rate, Parts | 3.4 | N/A | 4.2 | N/A |

[1]Isobutane Feed is the total isobutane feed to reactors #1 and #2, including recycle isobutane.

Although specific embodiments of peroxidation reactors and methods for using same have been depicted in the figures and described above, it will be understood with benefit of the present disclosure that a wide variety of alternative embodiments including different reactor and process designs may be employed. In this regard, benefits of one or more secondary liquid product outlets as described above may be realized in any peroxidation reactor in which a liquid product is taken from one or more main liquid product outlets positioned at a distance above the secondary product outlet. Typically such reactor vessels include one or more weirs for maintaining reactant liquid levels within the reactor and for encouraging separation of vapor reactant from liquid reactant. However, weirs are not necessary. Furthermore, it will be understood with benefit of the present disclosure that benefits of the disclosed method and apparatus may be obtained in a peroxidation reactor having any number of vapor and/or liquid outlets.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed methods and apparatus may be utilized in various combinations and/or independently. Thus the invention is not limited to only those combinations shown herein, but rather may include other combinations.

What is claimed is:

1. A process for producing peroxide in a reaction vessel, comprising:

introducing an organic compound and oxygen into said reaction vessel so that said organic compound and oxygen react to form peroxide;

withdrawing a first liquid product stream comprising peroxide from adjacent the top of the reaction vessel; and withdrawing a second liquid product stream comprising peroxide from adjacent the bottom of the reaction vessel.

2. The process of claim 1, wherein said organic compound is at least one of alkane having from about 4 to about 8 carbon atoms or derivatives thereof, alkyl aryl compound with one or more alkyl groups having from about 2 to about 8 carbon atoms or derivatives thereof, or a mixture thereof.

3. The process of claim 1, wherein said organic compound is at least one of isobutane, isopentane, iso-octane, cyclohexane, ethylbenzene, or a mixture thereof.

4. The process of claim 1, wherein said organic compound is an alkane having from about 4 to about 8 carbon atoms.

5. The process of claim 4, wherein said step of introducing comprises sparging a mixture of said organic compound and said oxygen to a point adjacent said bottom of said reaction vessel, and further comprises centrally charging a downwardly flowing stream of cooled isobutane to the top of the reaction vessel to induce central downflow of the isobutane and annular upflow of the sparged mixture and said recycle stream.

6. The process of claim 5, further comprising the step of charging a reaction mixture recycle stream to the reaction vessel above the sparge point.

7. The process of claim 4, further comprising the step of withdrawing a vapor product stream comprising said alkane from the top of the reaction vessel.

8. The process of claim 4, wherein said first liquid product stream and said second liquid product stream are withdrawn from said reaction vessel in a draw-off ratio of from about 4:1 to about 100:1.

9. The process of claim 1, wherein said reaction vessel is a vertical reactor having length to diameter ratio of at least about 1.1.

10. The process of claim 1, wherein said organic compound is isobutane and said peroxide is tertiary butyl hydroperoxide.

11. The process of claim 10, wherein said first and second liquid product streams comprise isobutane, tertiary butyl hydroperoxide, tertiary butyl alcohol and oxygenated hydrocarbon by-products.

12. The process of claim 10, further comprising the step of maintaining a temperature within said reaction vessel of between about 120° C. and about 165° C., and maintaining a pressure within said reaction vessel of between about 380 psig and about 600 psig.

13. The process of claim 10, further comprising the step of maintaining a temperature within said reaction vessel of between about 120° C. and about 165° C., and maintaining a pressure within said reaction vessel of between about 500 psig and about 600 psig.

14. A process for producing tertiary butyl hydroperoxide in a reaction vessel, comprising:
introducing liquid isobutane and oxygen into said reaction vessel so that said liquid isobutane and said oxygen react to form tertiary butyl hydroperoxide;
withdrawing a vapor product stream comprising isobutane from the top of the reaction vessel;
withdrawing a first liquid product stream comprising tertiary butyl hydroperoxide from adjacent the top of the reaction vessel; and
withdrawing a second liquid product stream comprising tertiary butyl hydroperoxide from adjacent the bottom of the reaction vessel.

15. The process of claim 14, wherein said step of introducing comprises sparging a mixture of said liquid isobutane and said oxygen to a point adjacent said bottom of said reaction vessel, and further comprises centrally charging a downwardly flowing stream of cooled isobutane to the top of the reaction vessel to induce central downflow of the isobutane and annular upflow of the sparged mixture and said recycle stream.

16. The process of claim 15, further comprising the step of charging a reaction mixture recycle stream to the reaction vessel above the sparge point.

17. The process of claim 14, wherein said first liquid product stream and said second liquid product stream are withdrawn from said reaction vessel in a draw-off ratio of from about 4:1 to about 100:1.

18. The process of claim 14, wherein said reaction vessel is a vertical reactor having length to diameter ratio of at least about 1.1.

19. The process of claim 14, wherein said reaction vessel is a vertical reactor having a length to diameter ratio of from about 1.1 to about 3.

20. The process of claim 14, wherein said first and second liquid product streams comprise isobutane, tertiary butyl hydroperoxide, tertiary butyl alcohol and oxygenated hydrocarbon by-products.

21. The process of claim 14, further comprising the step of maintaining a temperature within said reaction vessel of between about 120° C. and about 165° C., and maintaining a pressure within said reaction vessel of between about 500 psig and about 600 psig.

22. A process for the production of tertiary butyl hydroperoxide and tertiary butyl alcohol from isobutane and oxygen in a vertical reactor which comprises the steps of:
sparging a mixture of isobutane with oxygen at a point adjacent the bottom of the reactor,
charging a reaction mixture recycle stream to the reactor above the sparge point,
centrally charging a downwardly flowing stream of cooled isobutane adjacent the top of the reactor to induce central downflow of the isobutane and annular upflow of the sparged mixture and said recycle stream,
withdrawing a first liquid product stream adjacent the top of the reactor,
withdrawing a second liquid product stream adjacent the bottom of the reactor,
withdrawing a vapor product stream comprising isobutane from the top of the reactor,
partially condensing the vapor stream,
recycling the condensed isobutane to the bottom of the reactor, and recovering the first and second liquid product streams.

23. The process of claim 22, wherein said vertical reactor has a length to diameter ratio of at least about 1.1, wherein said step of charging a reaction mixture includes charging a reaction mixture recycle stream into said reactor adjacent the bottom thereof and above the sparging point for the said mixture of isobutane with oxygen, wherein said step of centrally charging includes the step of centrally charging an isobutane charge stream having a charge stream temperature of about 10° C. to about 55° C. to said reactor, wherein said step of withdrawing a liquid product stream comprises withdrawing a liquid product stream adjacent the top of said reactor comprising isobutane, tertiary butyl hydroperoxide, tertiary butyl alcohol and oxygenated hydrocarbon by-products, wherein said step of withdrawing a vapor product stream comprises withdrawing a vapor product stream from the top of said reactor comprising isobutane and entrained normally liquid reaction products, wherein said step of partially condensing comprises cooling said vapor product to condense normal liquid reaction product components thereof, wherein said step of recycling comprises recycling said condensed products to said reactor as said reaction mixture reflux stream, and further comprising the steps of:

establishing reaction conditions within said reactor including a temperature within the range of about 120° C. to about 165° C. and a pressure between about 500 psig and about 600 psig; and recycling uncondensed components of said product vapor stream comprising isobutane to said reactor in admixture with added oxygen as said sparge mixture.

24. A process for the non-catalytic or auto-catalytic production of tertiary butyl hydroperoxide and tertiary butyl alcohol from isobutane in a vertical reactor having a length to diameter ratio of from about 1.1 to about 3 to 1 which comprises the steps of:

establishing reaction conditions within said reactor including a temperature within the range of about 120° C. to about 165° C. and a pressure within the range of about 380 to about 600 psig, peripherally sparging about 200 to about 400 parts per hour of a mixture comprising oxygen and isobutane into said reactor adjacent the bottom thereof, said mixture containing 5 to about 15 parts of oxygen per 100 parts of isobutane, charging about 150 to about 250 parts per hour of a reaction mixture recycle stream into said reactor adjacent the bottom thereof and above the sparging point for the said mixture of isobutane with oxygen, centrally charging about 100 parts per hour of an isobutane charge stream having a charge stream temperature of about 10° C. to about 55° C. to said reactor adjacent the top thereof in a downwardly flowing direction to induce central downflow of said isobutane in said reactor and to thereby induce annular upflow of said sparged mixture and said reaction mixture recycle stream, withdrawing about 80 to about 120 parts per hour of a first liquid product stream adjacent the top of said reactor comprising isobutane, tertiary butyl hydroperoxide, tertiary butyl alcohol and oxygenated hydrocarbon by-products, withdrawing about 1 to about 20 parts per hour of a second liquid product stream adjacent the bottom of said reactor comprising isobutane, tertiary butyl hydroperoxide, tertiary butyl alcohol and oxygenated hydrocarbon by-products, withdrawing about 350 to about 650 parts per hour of a vapor product stream from the top of said reactor comprising isobutane and entrained normally liquid reaction products, cooling said vapor product to condense normal liquid reaction product components thereof, recycling said condensed products to said reactor as said reaction mixture recycle stream, recycling uncondensed components of said product vapor stream comprising isobutane to said reactor in admixture with added oxygen as said sparge mixture, and recovering said first and second liquid product streams.

25. The process of claim 24 wherein the first and second liquid product streams comprise about 10 to about 25 wt. % of tertiary butyl hydroperoxide, about 9 to about 20 wt. % of tertiary butyl alcohol, about 20 to about 75 wt. % of unreacted isobutane and about 2 to about 10 wt. % of oxygen-containing impurities including ditertiary butyl peroxide, methanol, methyl formate, acetone and water.

26. The process of claim 24, wherein the step of establishing includes the step of establishing a pressure of between about 500 psig and about 600 psig in said reactor.

27. The process of claim 1, wherein said peroxide comprises alkyl peroxide, alkyl aryl peroxide, or a mixture thereof.

\* \* \* \* \*